US009277978B2

(12) United States Patent
Williams et al.

(10) Patent No.: US 9,277,978 B2
(45) Date of Patent: Mar. 8, 2016

(54) DISPOSABLE DENTAL VALVE DEVICE

(71) Applicant: Stoma Ventures, LLC, St. Louis, MO (US)

(72) Inventors: Eric Williams, San Jose, CA (US); Mark Ellis, Oak Park, MI (US)

(73) Assignee: STOMA VENTURES, LLC, St. Louis, MI (US)

( * ) Notice: Subject to any disclaimer, the term of this patent is extended or adjusted under 35 U.S.C. 154(b) by 0 days.

(21) Appl. No.: 14/080,747

(22) Filed: Nov. 14, 2013

(65) Prior Publication Data

US 2014/0170595 A1 Jun. 19, 2014

Related U.S. Application Data

(60) Provisional application No. 61/726,654, filed on Nov. 15, 2012, provisional application No. 61/793,885, filed on Mar. 15, 2013.

(51) Int. Cl.
*F16K 5/00* (2006.01)
*A61C 17/06* (2006.01)
*A61C 1/00* (2006.01)

(52) U.S. Cl.
CPC .............. *A61C 17/04* (2013.01); *A61C 1/0061* (2013.01)

(58) Field of Classification Search
CPC .... A61C 1/0061; A61C 17/043; A61C 17/04; Y10S 251/904; F16K 27/065
USPC .................. 137/315.17; 251/309, 904; 433/95
See application file for complete search history.

(56) References Cited

U.S. PATENT DOCUMENTS

| 3,481,367 | A | * | 12/1969 | Deuschle | 137/625.47 |
| 3,536,101 | A | * | 10/1970 | Bosworth | 137/315.17 |
| 3,991,975 | A | * | 11/1976 | Sibrava | 251/317 |
| 4,580,978 | A |   | 4/1986 | Motola et al. |  |
| 4,861,266 | A | * | 8/1989 | Ashiku | 433/95 |
| 4,890,817 | A | * | 1/1990 | Uri | 251/312 |
| 4,966,551 | A | * | 10/1990 | Betush | 433/95 |
| 5,061,180 | A | * | 10/1991 | Wiele | 433/91 |
| 5,144,972 | A | * | 9/1992 | Dryden | 137/15.18 |
| 5,295,830 | A | * | 3/1994 | Shen et al. | 433/116 |
| 5,480,124 | A | * | 1/1996 | Bartlett et al. | 251/309 |
| 5,882,194 | A | * | 3/1999 | Davis et al. | 433/29 |
| 7,131,839 | B2 | * | 11/2006 | March | 433/95 |
| 2003/0014842 | A1 |   | 1/2003 | Niendorf |  |
| 2008/0121297 | A1 | * | 5/2008 | Indigne | 137/625.47 |
| 2012/0259300 | A1 | * | 10/2012 | Bjerregaard | 604/327 |
| 2013/0004585 | A1 |   | 1/2013 | Crudden et al. |  |

* cited by examiner

*Primary Examiner* — John K Fristoe, Jr.
*Assistant Examiner* — Reinaldo Sanchez-Medina
(74) *Attorney, Agent, or Firm* — David H. Chervitz

(57) ABSTRACT

A disposable dental valve device is disclosed which comprises a valve body having a tip receiving end, a hose receiving end, a lumen formed between the tip receiving end and the hose receiving end, and a partial opening formed in the valve body, and a rotatable valve sealing body adapted to being inserted into the partial opening, the rotatable valve sealing body having a bore for alignment with the lumen formed between the tip receiving end and the hose receiving end, the rotatable valve body having a top and a handle portion connected to the top.

20 Claims, 12 Drawing Sheets

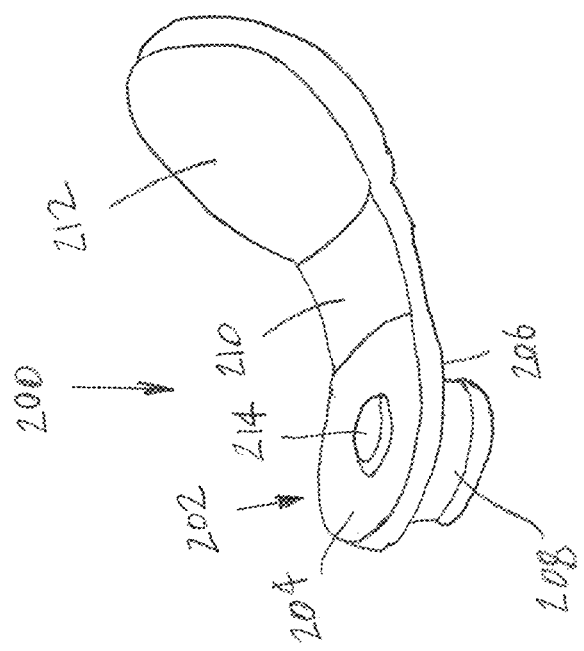

DISPOSABLE DENTAL VALVE DEVICE

RELATED APPLICATION

This application claims priority to U.S. Provisional Patent Application Ser. No. 61/726,654, filed on Nov. 15, 2012, and U.S. Provisional Patent Application Ser. No. 61/793,885, filed on Mar. 15, 2013, the disclosures of which are incorporated herein by reference.

BACKGROUND

This disclosure relates to a valve for a dental instrument and more particularly to a disposable valve device for a high volume evacuator or a low volume evacuator (saliva ejector).

During a dental procedure it is important to be able to remove saliva, blood, tooth fragments, metals, and other debris from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector. A saliva ejector typically comprises a plastic flexible tube for placement in the mouth of a patient. The saliva ejector tube is connected to a valve which in turn is connected to a source of vacuum. In this manner, saliva is passed through the ejector tube and the valve to be disposed of in a sanitary manner. Once the procedure is completed, the ejector should be discarded and the valve should be sterilized by autoclaving to be used again. Although it is suggested to autoclave the valve after use, it is known that autoclaving is hardly ever done. Another device that is capable of removing solid materials is a high volume evacuator system. A high volume evacuator system generally consists of a tube that may be inserted into a mouth of a patient with the tube connected to a valve which is connected to a source of vacuum. Again, in this manner, debris may be removed from the mouth of the patient. After the dental procedure, the tube is disposed of and the valve should be sterilized for reuse. However, although it is suggested to sterilize the valve after use, it is known that this suggested procedure is hardly ever followed. As can be appreciated, the saliva ejector and the high volume evacuator are used to remove liquids and debris from a mouth of a patient to prevent a patient from swallowing or aspirating liquids and debris produced during a dental procedure.

The saliva ejector valve and the high volume evacuator valve each has a valve body having a passage and a valve sealing member. The valve sealing member has an opening that may be aligned with the passage to allow saliva and other material to pass when the valve sealing member is in an open position. When the valve sealing member is in a closed position, the source of vacuum is cut off by the valve sealing member blocking the passage through the valve body. In this manner, the saliva ejector valve and the high volume evacuator valve may be opened or closed. However, due to the construction of the valve sealing member, an opening is formed through the valve body that is perpendicular to the passage formed in the valve body. In this manner, the valve sealing member is inserted into the opening from either end of the opening when the valve is assembled.

Although these devices and systems are beneficial, one disadvantage associated with their use is that the valves may become clogged with debris during use causing the valve to malfunction. It will then be required to disassemble the valve to remove the debris. This results in a valve that cannot be used again until it is repaired and cleaned. It is also possible that debris will lodge inside the mechanism of the valve rendering the valve inoperable during a procedure. If this were to occur a new valve would have to replace the failed valve during a procedure. The valves invariably collect debris, body fluids, blood, and solids that adhere and accumulate upon the internal surfaces of the valve. The detritus that adheres to the internal surfaces of the valve can become a breeding ground for microbial contaminants. This buildup also contains microorganisms that remain in the valve system unless the valves are disassembled, the internal accumulated debris removed, and the valve sterilized.

As can be appreciated, if the valve is not cleaned and sterilized after each procedure there is the possibility of cross-contamination from one patient to another patient. In order to control infection and disease, the valve must be removed from service, disassembled, cleaned, sterilized, reassembled, checked, and then returned to service. To complicate matters, the valve may have various O-rings that need to be replaced in order for the valve to function properly. For example, the valve sealing member may include two O-rings that assist in holding the valve sealing member within the opening formed in the valve body. When disassembling the valve sealing member from the valve body, it is possible that the O-rings may become damaged. If this were to occur then the O-rings would have to be replaced. It is also possible that the O-rings may deteriorate over time and air may leak through the opening and the valve sealing member. If this were to occur then it is possible that the valve and the valve sealing member may malfunction during a dental procedure or operation. For example, the valve sealing member may be ejected from the valve body and any saliva, liquid, blood, or debris may spray out of the opening where the valve sealing member should be. Malfunctioning of the valve during an operation should be avoided because the operation will have to be paused or stopped and the operating room will have to be cleaned.

Another disadvantage of the use of a valve is that once a procedure is completed and the valve is removed, there is considerable noise generated by the source of vacuum. Although the source of vacuum may be turned off, the shutoff valve for the source of vacuum may be at a remote location. This results in having to leave the operating area to shut down the source of vacuum. Further, when the source of vacuum is required again, the shutoff valve will require being turned on again. For a system that does not have multiple shutoff valves this could impact other procedures that are pending. Also, if there is a local shutoff valve, this valve may not be in easy reach which would require moving from the patient.

As pointed out above, a further disadvantage associated with the use of these known valves is that there is the possibility of cross-contamination between patients and/or dental care professionals. In order to prevent cross-contamination it becomes necessary to process these valves by cleaning and decontamination. Cleaning requires that all of the debris be removed from the valve as well as any organic and inorganic contamination. Removal of debris and contamination may be achieved either by scrubbing with a surfactant, detergent, and water, or by an automated process using chemical agents. One example of an automated process is the use of an ultrasonic cleaner. The valve also needs to be sterilized after debris and contaminants are removed. Since the valves are constructed of metal they are heat-tolerant and may be sterilized by use of such methods such as steam under pressure (autoclaving), dry heat, or unsaturated chemical vapor. As can be appreciated, protecting against cross-contamination can be an expensive and time consuming proposition. Further, as noted above, the valves contain a number of O-rings that may need to be replaced. In order to accomplish this, an inventory of O-rings needs to be maintained. Also, in order to replace some of the O-rings, a lubricant may have to be used. Again, the lubricant will have to be inventoried so that a supply is readily available for use by service technicians. Having to inventory various supplies that may be required to service such valves is a cumbersome operation that many healthcare facilities may want to avoid.

Therefore, it would be desirable to have a valve for a dental instrument that is disposable and only intended for one time use. It would also be desirable to have a valve that has a valve sealing member that is secured in place so that the valve sealing member does not malfunction during a dental operation. It would also be advantageous to have a valve for a dental instrument that is easy to install on or remove from hosing for a source of vacuum. It would also be desirable to include a cap device to cover a source of vacuum when a valve is removed from a hose connected to a source of vacuum to reduce or eliminate any noise associated with the source of vacuum.

BRIEF SUMMARY

In one form of the present disclosure, a disposable dental valve device comprises a valve body having a tip receiving end, a hose receiving end, a lumen formed between the tip receiving end and the hose receiving end, and a partial opening formed in the valve body, and a rotatable valve sealing body adapted to being inserted into the partial opening, the rotatable valve sealing body having a bore for alignment with the lumen formed between the tip receiving end and the hose receiving end, the rotatable valve sealing body having a top and a handle portion connected to the top.

In another form of the present disclosure, a disposable dental valve device comprises a valve body having a tip receiving end, a hose receiving end, a lumen formed between the tip receiving end and the hose receiving end, a partial opening formed in the valve body with the partial opening having a bottom receiving end, and a rotatable valve sealing body adapted to being inserted into the partial opening and contacting the bottom receiving end, the rotatable valve body having a bore having a first concave opening and a second concave opening with the bore and the openings for alignment with the lumen formed between the tip receiving end and the hose receiving end, the first and second concave openings forming a lower annular ring for engagement with the bottom receiving end, the rotatable valve body having a top and a handle portion connected to the top with movement of the handle capable of positioning the bore in alignment with the lumen.

In yet another form of the present disclosure, a disposable dental valve device kit comprises a valve body having a tip receiving end, a hose receiving end, a lumen formed between the tip receiving end and the hose receiving end, and a partial opening formed in the valve body, a rotatable valve sealing body adapted to being inserted into the partial opening, the rotatable valve sealing body having a bore for alignment with the lumen formed between the tip receiving end and the hose receiving end, the rotatable valve sealing body having a top and a handle portion connected to the top, and a cap device for insertion into a hose connected to a source of vacuum.

The present disclosure provides a disposable dental valve device for a dental instrument that is suitable for one time use and may be discarded after use.

The present disclosure provides a disposable dental valve device that is easy to install on a hose connected to a source of vacuum and have a tip installed on another end of the device.

The present disclosure provides a valve for a dental instrument that is small, lightweight, easy to handle, easy to install, and easy to operate.

The present disclosure also provides a valve for a dental instrument which is of simple construction and design and which can be easily employed with highly reliable results.

The present disclosure is related to a disposable dental valve device that does not require sterilization and prevents against cross-contamination.

The present disclosure provides a disposable dental valve device that may have an antimicrobial agent or chemical incorporated into the device to prevent any bacterial growth on the device. The antimicrobial agent or chemical may also be a coating applied to the disposable dental valve device.

The present disclosure is related to a disposable dental valve device that may be constructed of plastic that is recyclable or biodegradable to reduce the cost of the device and to allow the device to be disposable and discarded after a single use.

The present disclosure provides a disposable dental valve device further includes a cap device that may be used to cap off a source of vacuum when the device is removed from a hose connected to the source of vacuum to reduce or eliminate any sound or noise associated with the source of vacuum.

The present disclosure is related to a disposable dental valve device that has a valve sealing body that is easy to manipulate during a dental operation to open or close the valve.

These and other advantages of the present disclosure will become apparent after considering the following detailed specification in conjunction with the accompanying drawings, wherein:

BRIEF DESCRIPTION OF THE DRAWINGS

FIG. 12 is a perspective view of cap device constructed according to the present disclosure.

DETAILED DESCRIPTION OF PREFERRED EMBODIMENTS

Figure 1:
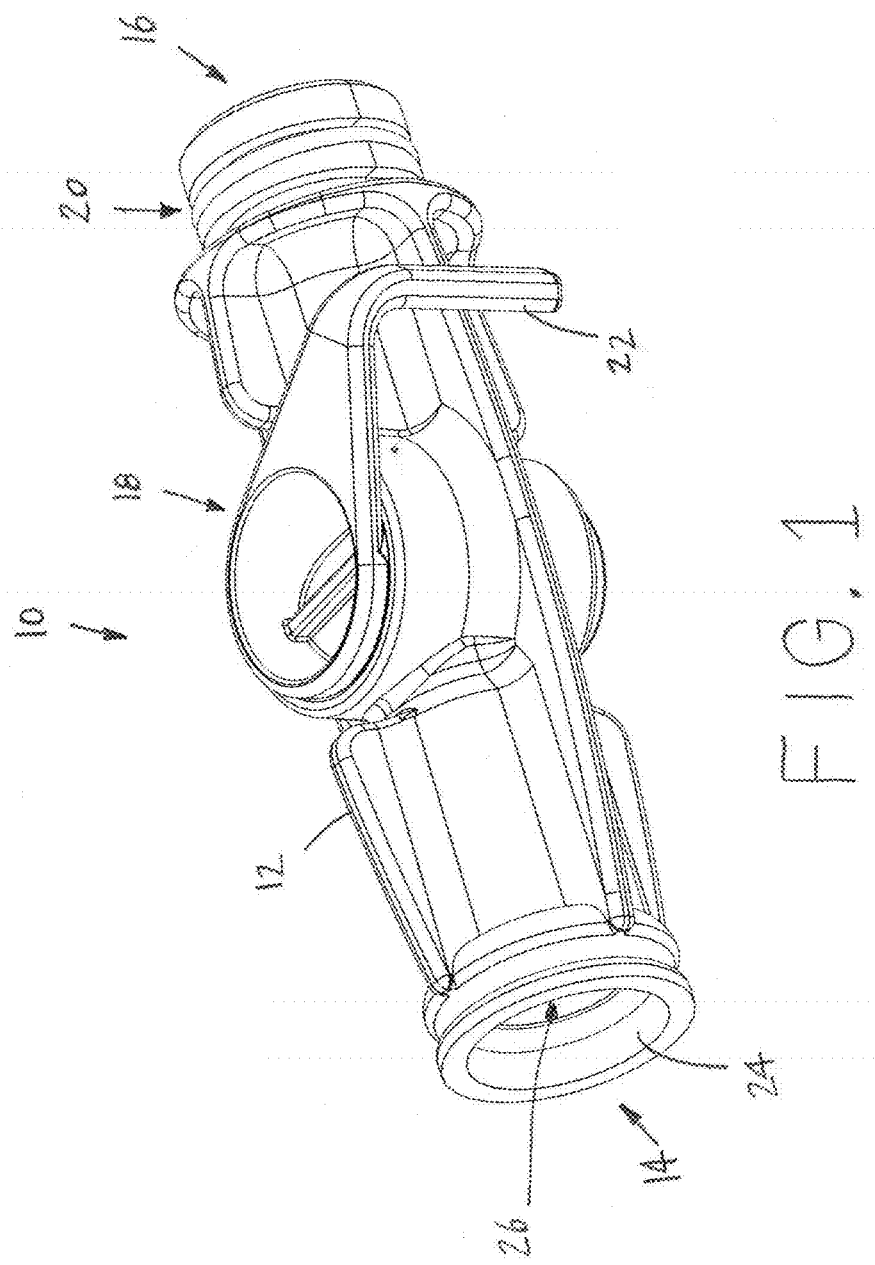
FIG. 1 is a perspective view of a disposable dental valve device constructed according to the present disclosure.

Referring now to the drawings, wherein like numbers refer to like items, number 10 identifies a disposable dental valve device for use with a dental system constructed according to the present disclosure. With reference now to FIG. 1, the valve 10 comprises a valve body 12 having a tip receiving end 14, a hose receiving end 16, and a rotatable valve sealing body 18. The tip receiving end 14 is adapted to receive an evacuator tip device (not shown) such as a high volume evacuator or a low volume evacuator (saliva ejector). The hose receiving end 16 is adapted to receive a vacuum line or a hose (not shown) which is connected to a suction system (also not shown). The hose receiving end 16 also has a circumferential channel 20 that is adapted to accept an O-ring (not shown). The O-ring is used to further secure a hose or a tailpiece to the hose receiving end 16. It is also possible that the hose receiving end 16 may incorporate a structure to secure a hose to the end 16 without the use of the channel 20 or the requirement for an O-ring. For example, the end 16 may be barbed so that the barbs may hold a hose thereon. The device 10 is constructed of material that allows the device 10 to be disposable and suitable for one time use. The device 10 also has a handle 22 for manual operation of the rotatable valve sealing body 18 of the device 10. Manual operation of the handle 22 will open the device 10, close the device 10, or partially open the device 10, as will be discussed more fully herein. As can be appreciated, a suction system provides suction through an evacuator tip device, the device 10, and a hose so that any debris or saliva that is introduced into an evacuator tip device is removed through an evacuator tip device, the valve 10, and a hose when the rotatable valve sealing body 18 of the device 10 is in an open state or a partially open state. The valve body 12 also has an opening 24 at the tip receiving end 14 and a passage or lumen 26 formed in the valve body 12. The lumen 26 continues through the valve body 12 to the hose receiving end 16. Although not shown, it is contemplated that the tip receiving end 14 may be constructed having an interior annular ring for receiving an O-ring to retain a tip therein. It is also possible that the tip receiving end 14 may have other structure that will allow a frictional engagement of a tip and the tip receiving end 14.

Figure 2:
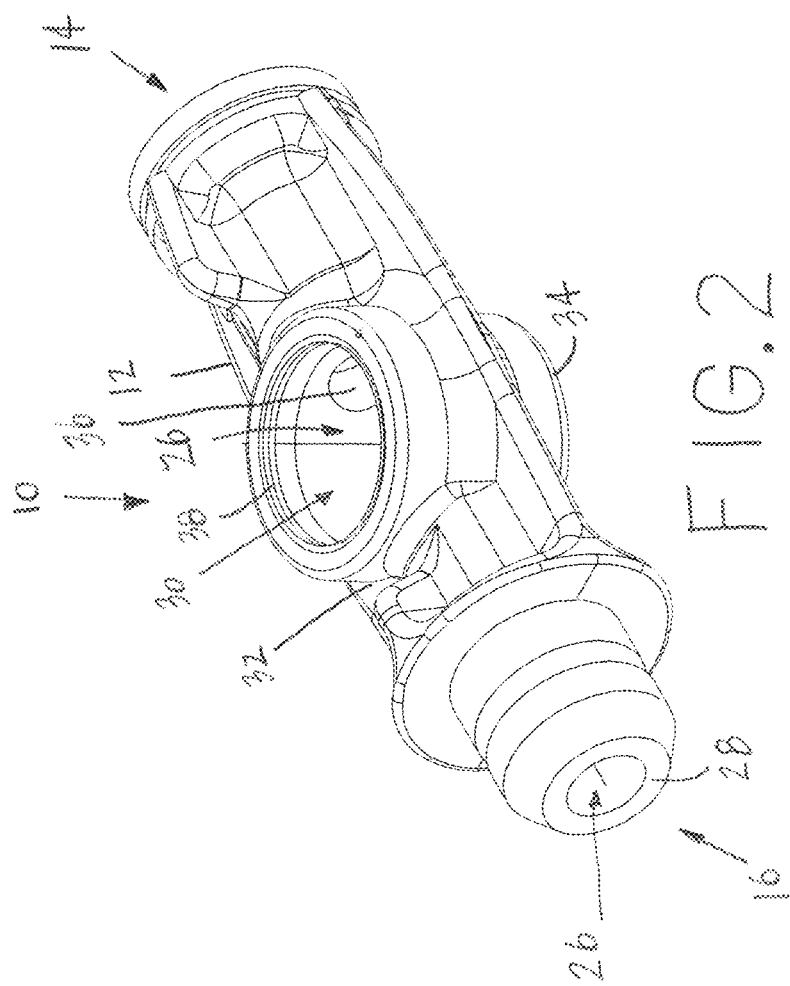
FIG. 2 is a perspective view of a disposable dental valve device constructed according to the present disclosure with a valve sealing body removed.

With reference now to FIG. 2, the device 10 is shown with the rotatable valve sealing device 18 being removed. The valve body 12 has the lumen 26 and an opening 28 at the hose receiving end 16. As has been described, the lumen 26 continues through the valve body 12 to the tip receiving end 14. The valve body 12 also has a partial opening 30 formed on a top side 32 of the valve body 12. The partial opening 30 does not go all the way through the valve body 12. The partial opening 30 is blocked by a bottom 34 of the valve body 12. An opening 36 is also shown in the lumen 26 between the tip receiving end 14 and the opening 30. An annular channel or ring 38 is formed in the opening 30 which is used to retain the rotatable valve sealing device 18 in place, as will be explained in further detail herein.

Figure 3:
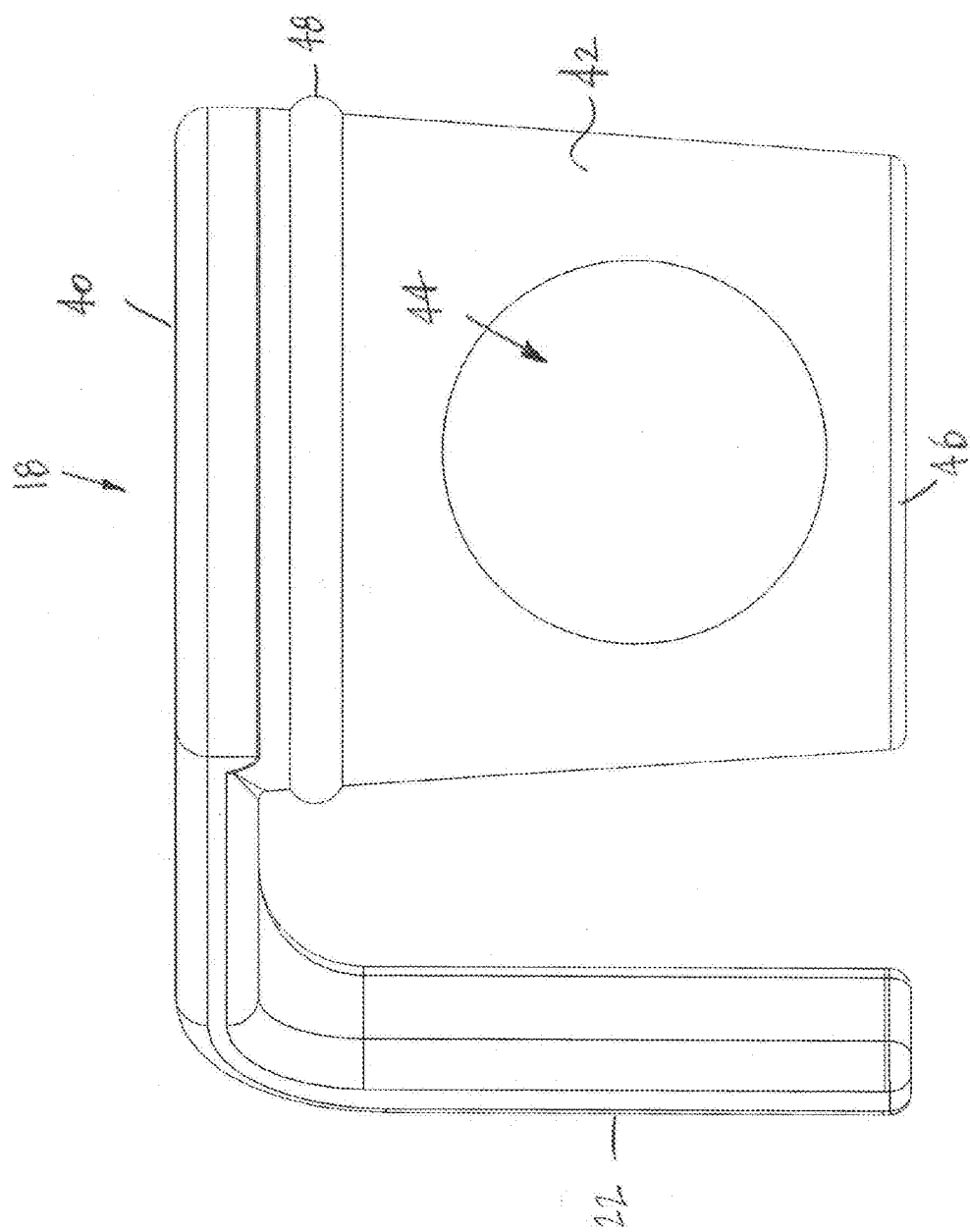
FIG. 3 a side perspective view of a valve sealing body constructed according to the present disclosure.

FIG. 3 shows the rotatable valve sealing body 18 in an open position. The rotatable valve sealing body 18 has a top 40, a central body portion 42 having a bore 44, and a bottom 46. The handle 22 is part of the top 40. The central body portion 42 also has an annular ridge portion 48 near the top 40. The ridge portion 48 is capable of fitting into the ring 38 (FIG. 2) in a snap fit engagement to secure the rotatable valve sealing body 18 within the valve body 12. The bore 44 is adapted to be aligned with the lumen 26 of the valve body 12. When the bore 44 is aligned with the lumen 26, the device 10 is in an open position and the source of vacuum will draw any fluid or debris from the tip receiving end 14 through the lumen 26 and the bore 44 and out through the hose receiving end 16. In this manner, fluid and debris may be removed from a mouth during a dental procedure or operation. Although the ridge 48 is shown, it is possible that an annular ring may be formed in the central body portion 42 and an O-ring may be used to hold the valve sealing body 18 in place. Also, although one ridge 48 is depicted, it is contemplated that another ridge 48 may be formed on the central body portion 42 near the bottom 46 and another ring 38 be formed in the opening 30 near the bottom 34 to receive the second ridge 48 to further secure the valve sealing body 18 in place.

Figure 4:
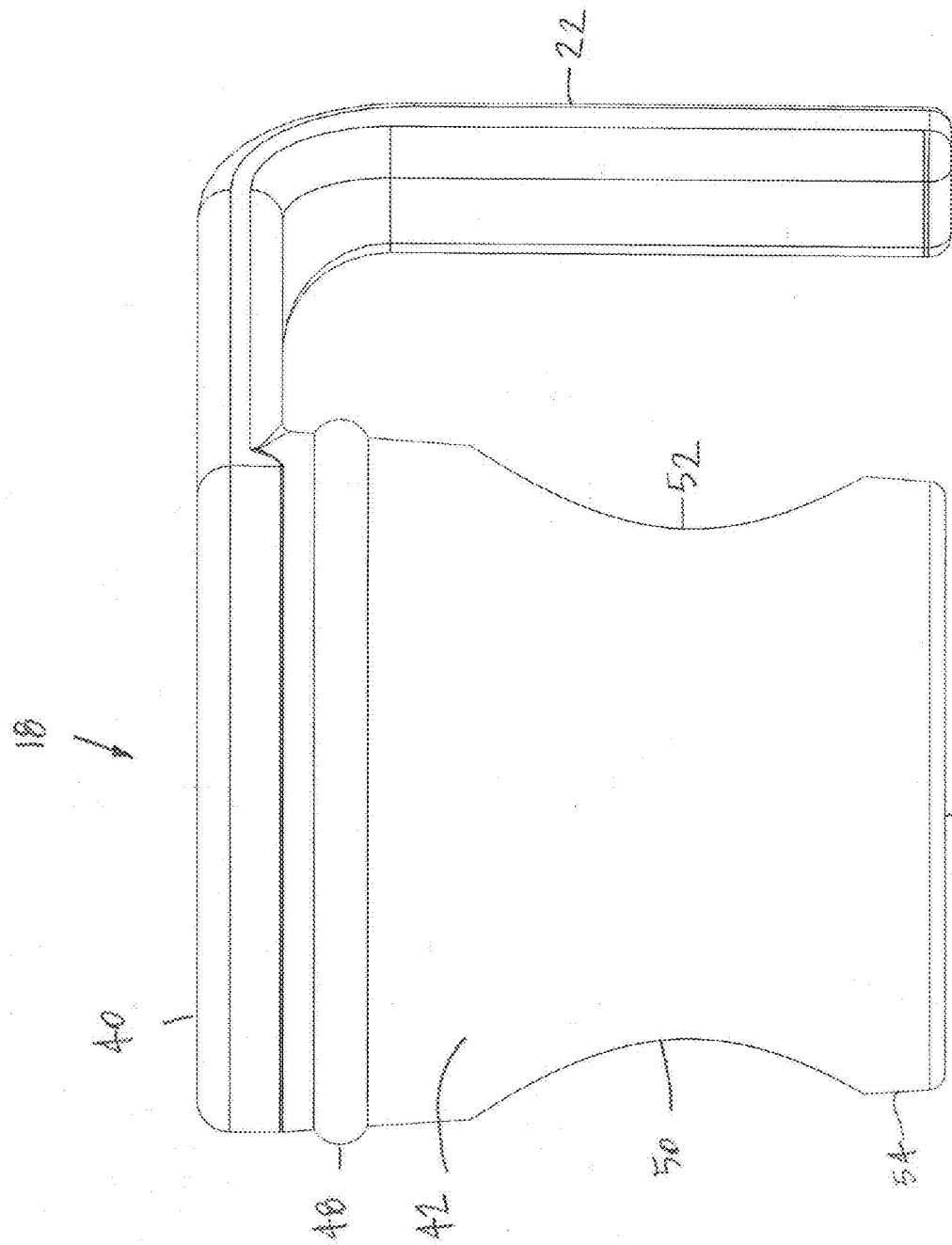
FIG. 4 is another side view of the valve sealing body constructed according to the present disclosure.

Referring now to FIG. 4, the rotatable valve sealing body 18 is illustrated in a closed position. The rotatable valve sealing body 18 has the top 40, the central body portion 42 having a first opening 50 and a second opening 52, and the bottom 46. The openings 50 and 52 are aligned with the bore 40 (FIG. 3). When the rotatable valve sealing body 18 is in the closed position, the central body portion 42 will block any air flow through the valve body 12. In essence, the bore 44 is no longer aligned with the lumen 26 formed in the valve body 12. The rotatable valve sealing body 18 is moved into the closed position by use of the handle 22. The openings 50 and 52 are concave and this provides a lower annular ring 54 that is formed in the sealing body 18.

Figure 5:
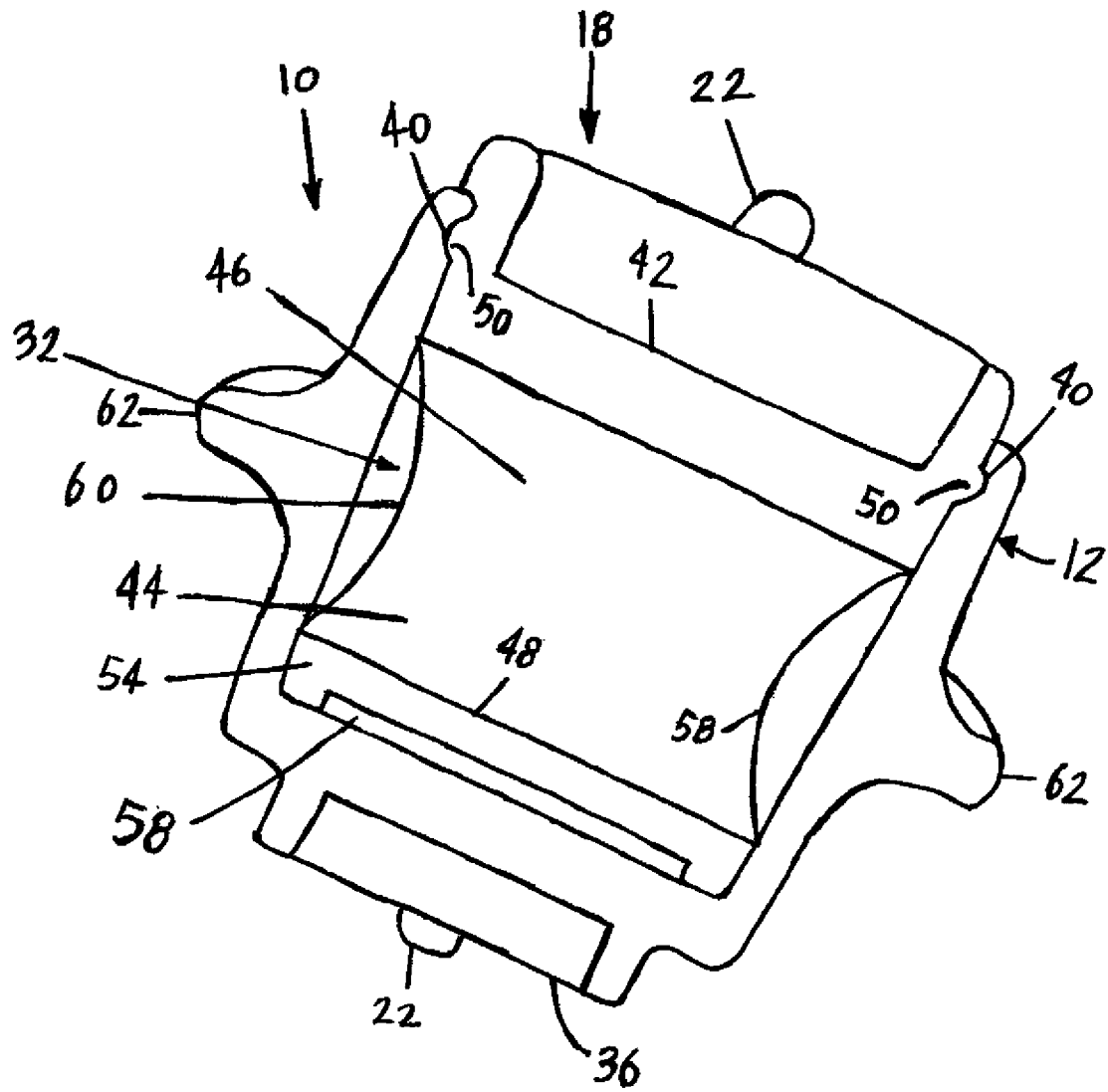
FIG. 5 is a cross-sectional view of the disposable dental valve device constructed according to the present disclosure.

FIG. 5 is a cross-sectional view of the disposable dental valve device 10 with the rotatable valve sealing body 18 in the closed position. The device 10 has the valve body 12 having the rotatable valve sealing body 18 mounted therein. The rotatable valve sealing body 18 is held in place by use of the ridge 48 being snapped into place within the ring 38. The bottom 46 of the rotatable valve sealing body 18 is adjacent to the bottom 34 of the valve body 12. In this manner, the rotatable valve sealing body 18 is able to rotate within the valve body 12. Further, the bottom 34 ensures that the opening 30 (FIG. 2) is a partial opening and the opening 30 does not go all the way through the valve body 12. The opening 30 reduces the risk that the rotatable valve sealing body 18 will become disengaged during use or that the valve 10 will fail during use. The rotatable valve sealing body 18 also has the bore 44 formed therein between the openings 50 and 52. As previously described, the openings 50 and 52 are concave and the sealing body 18 has the lower annular ring 54 that is frictionally engaged near the bottom 34 within the opening 30 formed in the valve body 12. The valve body 12 also has exterior ribs 56 that add strength to the valve body 12 and also assist in forming the valve body 12. The bottom 34 has a central indentation 58 formed within the annular ring 54. The handle 22 is also shown as being part of the device 10.

Figure 6:
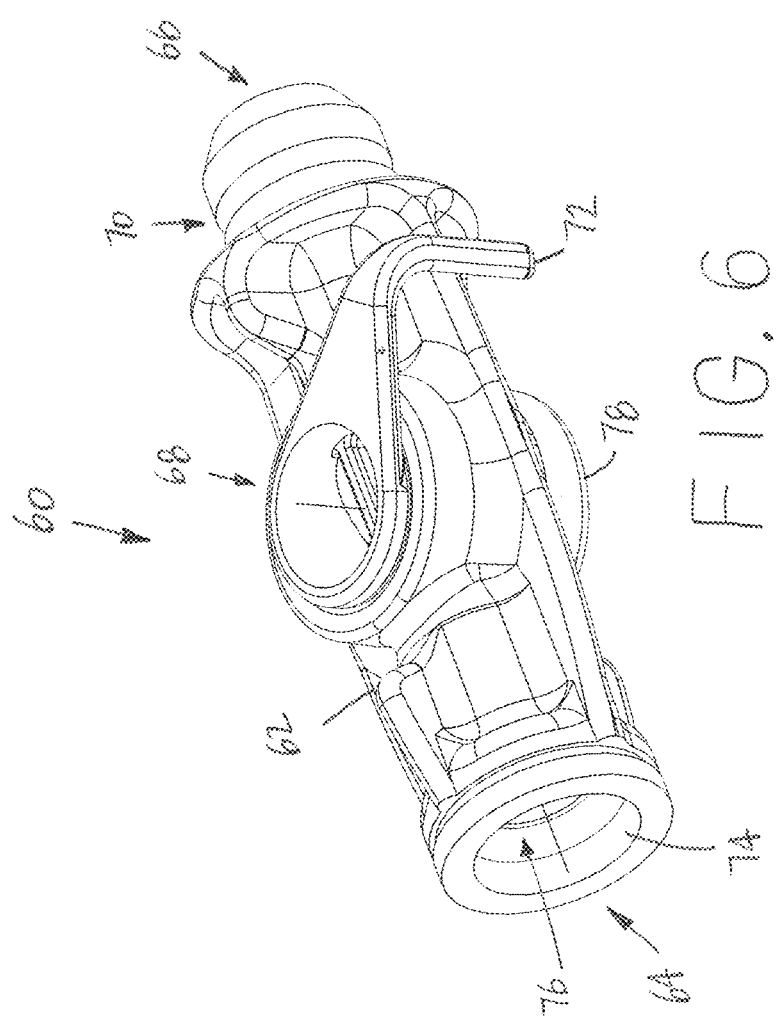
FIG. 6 is a perspective view of another embodiment of a disposable dental valve device constructed according to the present disclosure.

With reference now to FIG. 6, another embodiment of a disposable dental valve device 60 is shown. The valve 60 comprises a valve body 62 having a tip receiving end 64, a hose receiving end 66, and a rotatable valve sealing body 68. The tip receiving end 64 is adapted to receive an evacuator tip device (not shown) such as a low volume evacuator (saliva ejector). The hose receiving end 66 is adapted to receive a vacuum line or a hose (not shown) which is connected to a suction system (also not shown). The hose receiving end 66 also has a circumferential channel 70 that is adapted to accept an O-ring (not shown). The O-ring is used to further secure a hose or a tailpiece to the hose receiving end 66. It is also possible that the hose receiving end 66 may incorporate structure to secure a hose to the end 66 without the use of the channel 70 or the requirement for an O-ring. For example, the end 66 may be barbed so that the barbs may hold a hose thereon. The device 60 is constructed of material that allows the device 60 to be disposable and suitable for one time use. The device 60 also has a handle 72 for manual operation of the rotatable valve sealing body 68 of the device 60. Manual operation of the handle 22 will open the device 10, close the device 10, or partially open the device 10, as will be discussed more fully herein. As can be appreciated, a suction system provides suction through an evacuator tip device, the device 60, and a hose so that any debris or saliva that is introduced into an evacuator tip device is removed through an evacuator tip device, the valve 60, and a hose when the rotatable valve sealing body 68 of the device 60 is in an open state or a partially open state. The valve body 62 also has an opening 74 at the tip receiving end 64 and a passage or lumen 76 formed in the valve body 62. The lumen 76 continues through the valve body 62 to the hose receiving end 66. Although not shown, it is contemplated that the tip receiving end 64 may be constructed having an interior annular ring for receiving an O-ring to retain a tip therein. It is also possible that the tip receiving end 64 may have other structure that will allow a frictional engagement of a tip and the tip receiving end 64. The valve body 62 also has a bottom 78 that ensures that the valve body 62 only has a partial opening (not shown) for receiving the rotatable valve sealing body 68. In particular, the sealing body 68 does not go entirely through the valve body 62. One difference between the valve 60 and the valve 10 is that the valve 60 is smaller in size and is used to remove saliva from a mouth of a patient during a dental operation. Further, the hose receiving end 66 may be smaller to accommodate a smaller vacuum hose being attached thereto.

Figure 7:
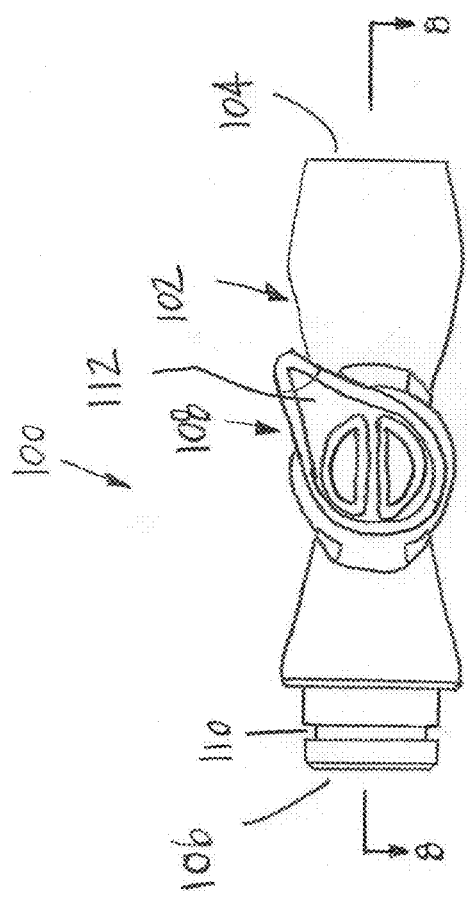
FIG. 7 is a top view of another embodiment of a disposable dental valve device constructed according to the present disclosure.

FIG. 7 illustrates another embodiment of a disposable dental valve device 100 constructed according to the present disclosure. The valve 100 comprises a valve body 102 having a tip receiving end 104, a hose receiving end 106, and a rotatable valve sealing body or member 108. The tip receiving end 104 is adapted to receive an evacuator tip device (not shown). The hose receiving end 106 is adapted to receive a vacuum line or a hose (not shown) which is connected to a suction system (also not shown). The hose receiving end 106 also has a circumferential channel 110 that is adapted to accept an O-ring (not shown). The O-ring is used to further secure a hose or a tailpiece to the hose receiving end 106. The device 100 is constructed of material that allow the device 100 to be disposable and suitable for one time use. The device 100 also has a handle 112 for manual operation of the rotatable valve sealing body 108 of the device 100. Manual operation of the handle 112 will open the device 100, close the device 100, or partially open the device 100, as will be discussed more fully herein. As can be appreciated, a suction system provides suction through an evacuator tip device, the device 100, and a hose so that any debris or saliva that is introduced into an evacuator tip device is removed through an evacuator tip device, the valve 100, and a hose when the device is in an open state or a partially open state.

Figure 8:
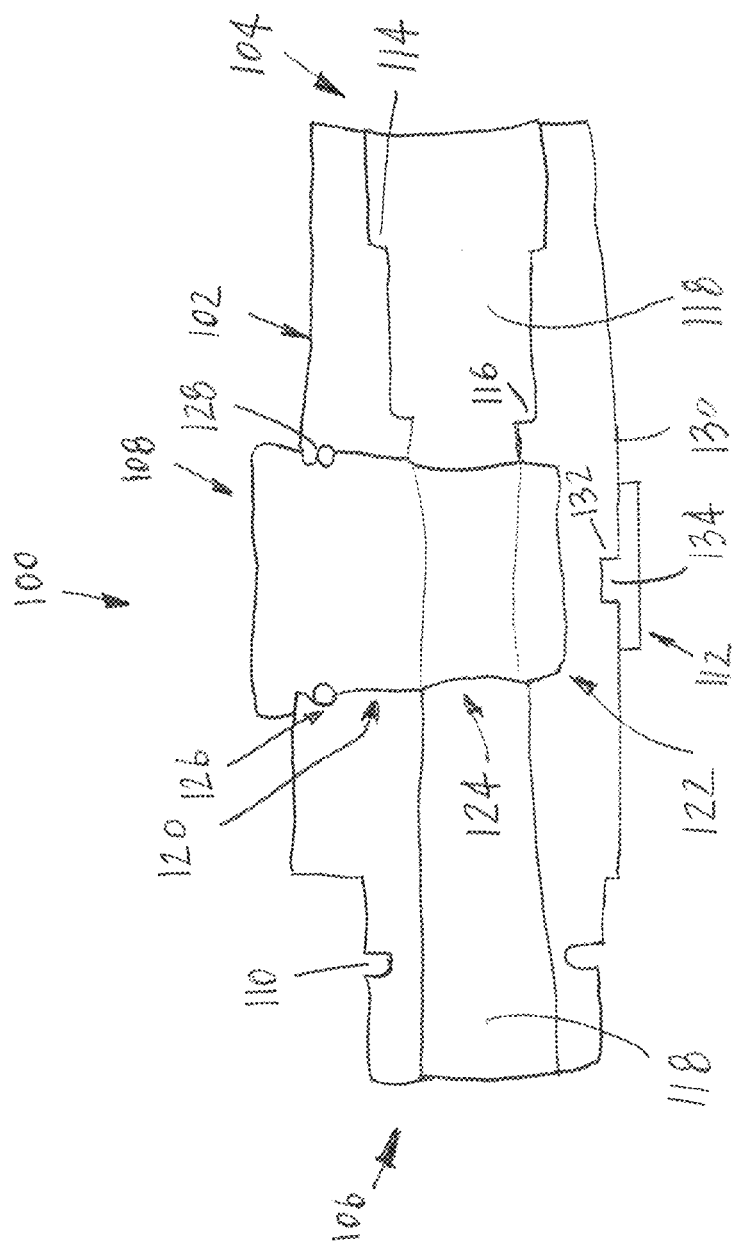
FIG. 8 is an enlarged cross-sectional view of the disposable dental valve device shown in FIG. 7 taken along the line of plane 8-8.

Referring now in particular to FIG. 8, a cross-sectional view of the disposable dental valve device 100 is shown. The device 100 comprises the valve body 102 having the tip receiving end 104, the hose receiving end 106, and the rotatable valve sealing body 108. The tip receiving end 104 has a first ledge portion 114 and a second ledge portion 116. The ledge portions 114 and 116 are used to capture or hold an evacuator tip that is inserted therein. In some cases, only the ledge portion 114 may be required to hold an evacuator tip within the tip receiving end 104. A duct or lumen 118 is formed in the valve body 102 between the tip receiving end 104 and the hose receiving end 106. A partial cavity 120 is formed in the valve body 102 and the lumen 118 and is used to capture and hold the rotatable valve sealing body 108. The valve body 102 has a bottom receiving end 122 that allows the rotatable valve sealing body 108 to rotate therein. In particular, the rotatable valve sealing body 108 does not go fully through the valve body 102. The rotatable valve sealing body 108 has a bore 124 formed therein. The bore 124 is capable of being in alignment with the lumen 118 to allow air, debris, saliva, blood, and liquid to pass through the device 100. Also, when the bore 124 is repositioned such that the bore 124 is not aligned with the lumen 118, air may not now pass through the device 100. In this particular orientation the device 100 is shut or closed. The valve body 102 also has a circumferential or annular channel 126 formed therein which is adapted to receive an O ring 128. The O ring 128 assists in securing or retaining the rotatable valve body 108 within the partial cavity 120. Although the O ring 128 is disclosed, it is also possible that the rotatable valve body 108 may incorporate a rib or ridge that fits into the channel 126.

The valve body 102 also has an exterior bottom side 130 that has an indentation 132 formed therein. The indentation 132 is adapted for receiving a tab portion 134 of the handle 112 the rotatable valve body 108. When the tab portion 134 is inserted into the indentation this facilitates a further securing point of the rotatable valve body 108 to the valve body 102. The tab portion 134 also assists in operating the rotatable valve body 108.

Figure 9:
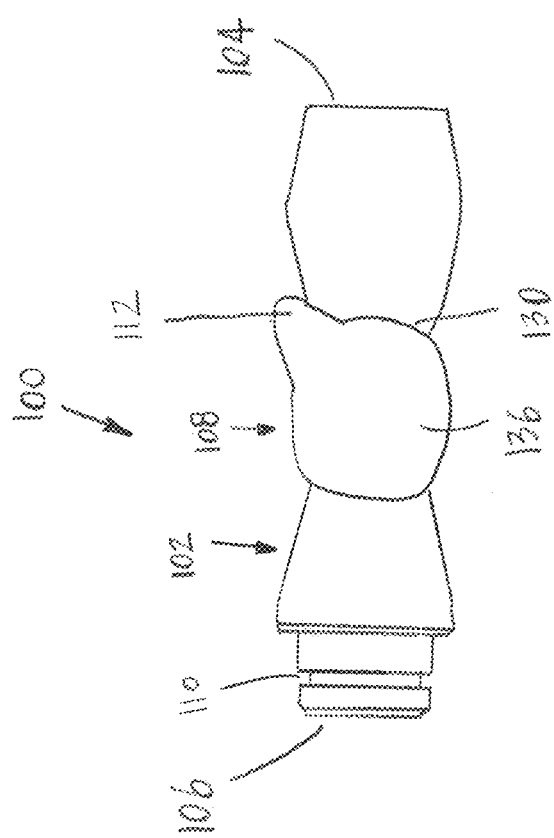
FIG. 9 is a bottom view of the disposable dental valve device constructed according to the present disclosure.

Referring now to FIG. 9, a bottom view of the device 100 is illustrated. The device 100 comprises the tip receiving end 104, the hose receiving end 106, and the rotatable valve sealing body 108. The hose receiving end 106 has the circumferential channel 110 that is formed therein. The rotatable valve sealing body 108 has a bottom end 136 that is connected to the handle 112. The bottom end 136 is in a snap fit engagement with the exterior bottom side 130 of the valve body 102.

Figure 10:
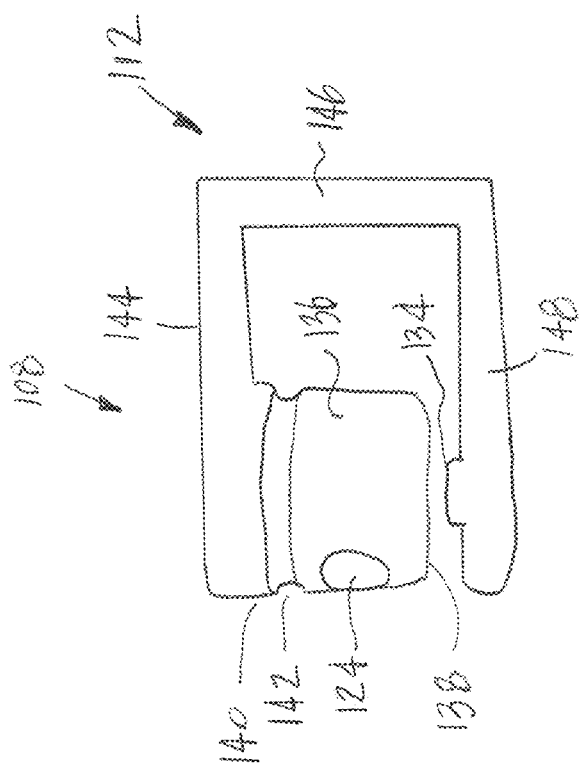
FIG. 10 is a perspective view of a rotatable valve body constructed according to the present disclosure.

FIG. 10 shows a perspective view of the rotatable valve sealing body 108 removed from the device 100. The rotatable valve sealing body 108 has a central body portion 136 that has the bore 124 formed therein. The central body portion 136 has a bottom 138 and a top 140. The central body portion 136 also has a circumferential channel 142 formed in or near the top 140. The channel 142 is adapted to receive the O ring 128 (FIG. 8). The handle 112 has a top portion 144, a central portion 146, and a bottom portion 148. The top portion 144, the central portion 146, and the bottom portion 148 form the handle 112. The bottom portion 148 also has the tab portion 134. The central portion 146 and the bottom portion 148 are resilient enough that these portions 146 and 148 may be manipulated to assemble the rotatable valve body 108 into the valve body 102.

Figure 11:
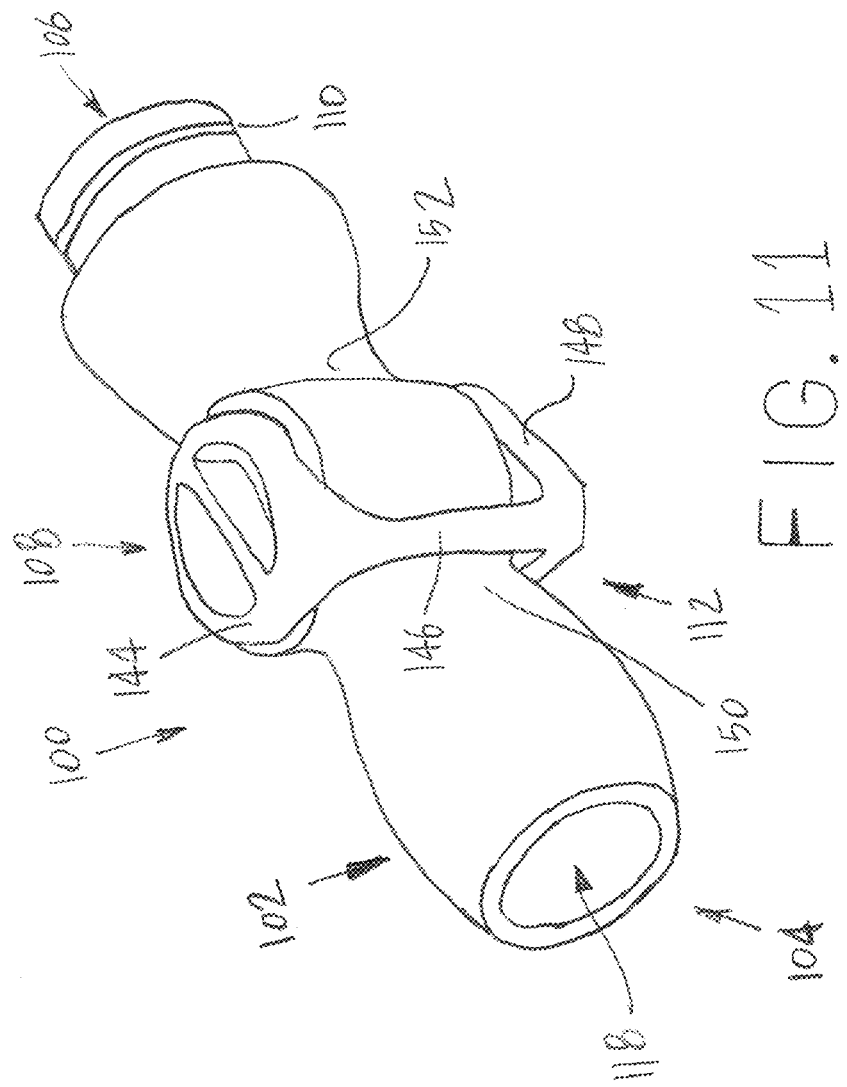
FIG. 11 is a perspective view of a disposable dental valve constructed according to the present disclosure for receiving a saliva ejector tip.

With particular reference now to FIG. 11, a perspective view of the disposable dental valve device 100 is depicted. The device 10 is shown to comprise the tip receiving end 104, the hose receiving end 106, and the rotatable valve sealing body 108. The hose receiving end 106 has the circumferential channel 110 that is formed therein. The lumen 118 is shown and it forms a channel or a path for debris and liquids to follow. The valve body 102 also has a tip end side 150 and a hose end side 152. The sides 150 and 152 form stops at which the central portion 146 of the handle 112 may not travel past. In this manner, the side 150 may indicate that the bore 124 of the rotatable valve body 108 is in the open position meaning that the bore 124 is in alignment with the lumen 118. Further, the side 152 may indicate that the bore 124 is not in alignment with the lumen 118 to indicate that the rotatable valve body 108 is in the closed position. The handle 112 may also be moved to a partially open position by moving the handle away from either of the sides 150 and 152. For example, the suction system may be too strong in the fully open position and a dentist may require less suction. By moving the handle 112 away from either of the sides 150 or 152 only a portion of the bore 124 is in alignment with the lumen 118. It is also possible to include indicia on the valve body 102 to indicate which direction or side 150 or 152 is the open or closed position.

FIG. 12 illustrates a cap device 200 is depicted which is used to be placed over the opening of a hose when the devices 10, 60, or 100 are removed from the hose to remove or dispose the devices 10, 60, or 100. In this manner, the opening of the hose will be physically blocked to shut off any air from rushing into the hose to silence any noise produced by the suction system or a source of vacuum. The cap device 200 is sized and shaped to fit over the opening of the hose. The cap device 200 may be constructed of any suitable material such as rubber or plastic. The valve devices 10, 60, and 100 may include the cap device 200 so that when valve devices 10, 60, or 100 are being removed from the hose for disposal after use the cap device 200 may be placed over the opening of the hose. The cap device 200 comprises a body portion 202 having a top side 204 and a bottom side 206 with the bottom side 206 having a plug portion 208. A central portion 210 is connected between the body portion 202 and a pull 212. The top side 204 has a raised portion or bump 214. The plug portion 208 is inserted into the opening of the hose or flexible tubing connected to a suction source. The pull 212 is used to be grasped by a hand to remove the plug portion 208 and the cap device 200 from the hose when a new disposable dental valve device 10, 60, or 100 is to be used. The plug portion 208 may be of a sufficient size and shape to plug an opening associated with a hose attached to a source of suction. The cap device 200 may also be provided separately from the devices 10, 60, or 100. As has been indicted above, it is also possible that the cap device 200 may be provided as a kit with the devices 10, 60, and 100.

Although not shown, it is also possible that the tip receiving end 14 may include an inlet end gasket, such as a balloon gasket, or an O ring for holding or securing an evacuator tip in place. However, it is also contemplated that the device 10 and an evacuator tip may be of unitary construction and provided as a single piece device. The inlet end gasket may fit within channels or grooves formed in the tip receiving end 14. It is also possible that the hose receiving end 16 may incorporate a hose adapter or a tailpiece for securing a flexible hose connected to a suction system.

In operation of for example the device 10, the hose receiving end 16 of the device 10 is placed on to a hose connected to a suction system and an evacuator tip inserted into the tip receiving end 14 and then placed in a mouth of a dental patient. The handle 22, which may include an indicium to indicate the closed position and the open position, is manually operated to open the device 10. Once in the open position, air is allowed to flow through the tip, the tip receiving end 14, the lumen 26, the bore 44 of the rotatable valve sealing body 18, the hose receiving end 16 and into a suction system. When suction is not needed during a dental procedure, the handle 22 is moved to the closed position. Further, once a dental procedure has been completed, the handle 22 is moved to the closed position, the device is easily separated from the hose, and the cap device 200 is placed over the opening associated with the hose. The cap device 200 will block any air from being sucked into the hose and this silences any noise that is generated by the source of vacuum or the suction system. Once the device 10 is disconnected from the hose, the device 10 may be disposed of by any suitable manner. A new device 10 is then connected to the hose after the cap device 200 is removed. With the new valve 10 installed, another dental procedure may be initiated.

The disposable dental valve devices 10, 60, and 100 may be formed of any suitable material such as plastic, polyethylene, and high density polyethylene or any other suitable material that is disposable and recyclable. Any suitable plastic may be used to construct the devices 10, 60, and 100 so that the devices 10, 60, and 100 may withstand use in a dental operation or procedure. It is also possible and contemplated to incorporate an antimicrobial agent or chemical in the plastic or to provide a coating of an antimicrobial agent on the plastic to further prevent cross-contamination when using the devices 10, 60, and 100.

From all that has been said, it will be clear that there has thus been shown and described herein a disposable dental valve device which fulfills the various advantages sought therefore. It will become apparent to those skilled in the art, however, that many changes, modifications, variations, and other uses and applications of the subject disposable dental valve device are possible and contemplated. All changes, modifications, variations, and other uses and applications which do not depart from the spirit and scope of the disclosure are deemed to be covered by the disclosure, which is limited only by the claims which follow.

What is claimed is:

1. A disposable dental valve device comprising:
a valve body having an interior, a tip receiving end, a hose receiving end, a lumen formed between the tip receiving end and the hose receiving end, and a partial opening formed in the valve body with an annular channel formed in the interior and the interior having a bottom receiving end having a flat surface; and
a rotatable valve sealing body adapted to being inserted into the partial opening, the rotatable valve sealing body having a bore for alignment with the lumen formed between the tip receiving end and the hose receiving end, the rotatable valve sealing body having a top having an annular ridge portion and a handle portion connected to the top, the annular ridge portion for insertion into the annular channel formed in the interior of the valve body to secure the rotatable valve sealing body within the valve body, the rotatable valve sealing body having a central body portion having an exterior surface, an upper end below the annular ridge portion, and a lower end having an annular ring having a surface and a central indentation formed within the annular ring between the surface of the annular ring with the surface of the annular ring contacting the flat surface of the bottom receiving end.

2. The disposable dental valve device of claim 1 wherein the rotatable valve sealing body and the valve body are each constructed of plastic.

3. The disposable dental valve device of claim 1 wherein the valve body comprises an exterior rib extending from the tip receiving end to the partial opening formed in the valve body.

4. The disposable dental valve device of claim 1 wherein the valve body further comprises an exterior rib extending from the hose receiving end to the partial opening formed in the valve body.

5. The disposable dental valve device of claim 1 wherein the valve body further comprises a first exterior rib extending from the hose receiving end to the tip receiving end, a second exterior rib extending from the hose receiving end to the tip receiving end, a third exterior rib extending from the hose receiving end to the partial opening formed in the valve body, a fourth exterior rib extending from the hose receiving end to the partial opening formed in the valve body, a fifth exterior rib extending from the tip receiving end to the partial opening formed in the valve body, and a sixth exterior rib extending from the tip receiving end to the partial opening formed in the valve body.

6. The disposable dental valve device of claim 1 wherein an antimicrobial agent is incorporated into the disposable dental valve device.

7. The disposable dental valve device of claim 1 wherein the valve body further comprises an exterior rib formed from the tip receiving end to the hose receiving end.

8. A disposable dental valve device comprising: a valve body having an interior having an annular channel formed in the interior, tip receiving end, a hose receiving end, a lumen formed between the tip receiving end and the hose receiving end, a partial opening formed in the valve body with the partial opening having a bottom receiving end having a flat surface; and a rotatable valve sealing body adapted to being inserted into the partial opening and contacting the bottom receiving end, the rotatable valve body having a bore having a first concave opening and a second concave opening with the bore and the openings for alignment with the lumen formed between the tip receiving end and the hose receiving end, the first and second concave openings forming a lower annular ring having a surface for engagement with the flat surface of the bottom receiving end and the interior of the valve body, the rotatable valve body having a top having an annular ridge portion with the annular ridge portion for insertion into the annular channel formed in the interior of the valve body to secure the rotatable valve sealing body within the valve body and a handle portion connected to the top with movement of the handle capable of positioning the bore in alignment with the lumen, the rotatable valve sealing body having a central body portion having an exterior surface, an upper end below the annular ridge portion, and a lower end having the lower annular ring having the surface and having a central indentation formed within the annular ring between the surface of the annular ring with the surface of the annular ring contacting the flat surface of the bottom receiving end.

9. The disposable dental valve device of claim 8 wherein the valve body further comprises an exterior rib extending from the tip receiving end to the partial opening formed in the valve body.

10. The disposable dental valve device of claim 8 wherein the valve body further comprises an exterior rib extending from the hose receiving end to the partial opening formed in the valve body.

11. The disposable dental valve device of claim 8 wherein the valve body further comprises a first exterior rib extending from the hose receiving end to the tip receiving end, a second exterior rib extending from the hose receiving end to the tip receiving end, a third exterior rib extending from the hose receiving end to the partial opening formed in the valve body, a fourth exterior rib extending from the hose receiving end to the partial opening formed in the valve body, a fifth exterior rib extending from the tip receiving end to the partial opening formed in the valve body, and a sixth exterior rib extending from the tip receiving end to the partial opening formed in the valve body.

12. The disposable dental valve device of claim 8 wherein an antimicrobial agent is incorporated into the disposable dental valve device.

13. The disposable dental valve device of claim 8 wherein the valve body further comprises a first exterior rib extending from the hose receiving end to the tip receiving end and a second exterior rib extending from the hose receiving end to the tip receiving end.

14. The disposable dental valve device of claim 8 wherein the disposable dental valve is constructed of plastic.

15. A disposable dental valve device kit comprising:
a valve body having an interior having an annular channel formed in the interior, a tip receiving end, a hose receiving end, a lumen formed between the tip receiving end and the hose receiving end, and a partial opening formed in the valve body and the interior having a bottom receiving end having a flat surface;
a rotatable valve sealing body adapted to being inserted into the partial opening, the rotatable valve sealing body having a bore for alignment with the lumen formed between the tip receiving end and the hose receiving end, the rotatable valve sealing body having a top having an annular ridge portion and a handle portion connected to the top, the annular ridge portion for insertion into the annular channel formed in the interior of the valve body to secure the rotatable valve sealing body within the valve body, the rotatable valve sealing body having a central body portion having an exterior surface, an upper end below the annular ridge portion, and a lower end having an annular ring having a surface and a central indentation formed within the annular ring between the surface of the annular ring with the surface of the annular ring contacting the flat surface of the bottom receiving end; and
a cap device for insertion into a hose connected to a source of vacuum.

16. The disposable dental valve device kit of claim 15 wherein the cap device comprises a body portion having a top side and a bottom side with the bottom side having a plug portion, a pull, and a central portion connected between the body portion and the pull.

17. The disposable dental valve device kit of claim 15 wherein the cap device is constructed of rubber.

18. The disposable dental valve device kit of claim 15 wherein the cap device is constructed of plastic.

19. The disposable dental valve device kit of claim 15 wherein an antimicrobial agent is incorporated into the cap device.

20. The disposable dental valve device kit of claim 15 wherein the valve body further comprises a first exterior rib extending from the hose receiving end to the tip receiving end, a second exterior rib extending from the hose receiving end to the tip receiving end, a third exterior rib extending from the hose receiving end to the partial opening formed in the valve body, a fourth exterior rib extending from the hose receiving end to the partial opening formed in the valve body, a fifth exterior rib extending from the tip receiving end to the partial opening formed in the valve body, and a sixth exterior rib extending from the tip receiving end to the partial opening formed in the valve body.

* * * * *